United States Patent [19]

Christensen et al.

[11] 4,138,547

[45] Feb. 6, 1979

[54] PROCESS FOR PREPARING 1,2,4-TRIAZOLE NUCLEOSIDES

[75] Inventors: Leon F. Christensen, Orem, Utah; Joseph T. Witkowski, Morris Township, Morris County, N.J.

[73] Assignee: ICN Pharmaceuticals, Inc., Irvine, Calif.

[21] Appl. No.: 863,293

[22] Filed: Dec. 22, 1977

[51] Int. Cl.$^2$ .................... C07H 17/00; C07H 19/06
[52] U.S. Cl. .................................. 536/23; 536/24; 536/26; 536/27; 536/28; 536/29
[58] Field of Search .................................. 536/23, 22

[56] References Cited

U.S. PATENT DOCUMENTS

| 3,798,209 | 3/1974 | Witkowski | 536/23 |
| 4,021,542 | 5/1977 | Schmidt | 536/22 |

*Primary Examiner*—Johnnie R. Brown
*Assistant Examiner*—Blondel Hazel
*Attorney, Agent, or Firm*—K. H. Boswell

[57] ABSTRACT

1-β-D-Ribofuranosyl-1,2,4-triazole-3-carboxamide is prepared by a process wherein a suitably substituted formimidic acid hydrazide is condensed with a blocked derivative of D-ribose and the intermediate is ring closed with a reagent which donates one carbon atom to yield a 3-substituted-1-(blocked β-D-ribofuranosyl)-1,2,4-triazole. Treatment of this intermediate with ammonia and/or removal of the blocking group yields the product.

4 Claims, No Drawings

PROCESS FOR PREPARING 1,2,4-TRIAZOLE NUCLEOSIDES

Cross Reference to Related Patents

This application is related to U.S. Patents 3,798,209 and 3,976,545 both assigned to the same assignee as this application, the disclosures of which are both expressly incorporated herein by reference.

Background of the Invention

The compound 1-β-D-ribofuranosyl-1,2,4-triazole-3-carboxamide has been found to be useful as an antiviral agent. This invention relates to a novel chemical method for the preparation of this nucleoside.

In our commonly assigned U.S. Pat. Nos. 3,798,209 and 3,976,545 the disclosures of which are herein expressly incorporated by reference, there are described chemical syntheses, an enzymatic synthesis and the antiviral activity of the compound 1-β-D-ribofuranosyl-1,2,4-triazole-3-carboxamide. The aforementioned chemical syntheses described in U.S. Pat. No. 3,798,209 utilizes procedures involving glycosylation of a preform triazole including 3-cyano-1,2,4-triazole which in turn was prepared from cyanoformimidic acid hydrazide and ethylorthoformate. The hydrazine derivative of 2,3-O-isopropylidene-D-ribose, Angew. Chem. Int. Ed., 14, 64 (1975), has been used to prepare pyrazole ribonucleosides; however, there is no published report of the use of it to prepare biologically active triazole nucleosides.

The present invention is a novel synthesis of triazole nucleosides wherein the triazole ring is formed from a formamidrazone isopropylidene ribose.

BRIEF SUMMARY OF THE INVENTION

1-β-D-Ribofuranosyl-1,2,4-triazole-3-carboxamide is prepared by reacting cyanoformimidic acid hydrazide, with D-ribose which has been suitably blocked to give a $N^1$-(blocked-D-ribofuranosyl) cyanoformamidrazone which is then ring closed with a one carbon atom donating reagent which is in the formic acid oxidization state to form a 3 cyano-1(β-D-blocked ribofuranosyl)-1,2,4-triazole which after ammonolysis and deblocking, yields the product.

In a preferred method of synthesis as shown in Scheme I, cyanoformimidic acid hydrazide is reacted with 2,3-O-isopropylidene-D-ribose to yield $N^1$-(2,3-O-isopropylidene-D-ribofuranosyl)cyanoformamidrazone which is ring closed with triethylorthoformate followed by treatment with ammonia and acid hydrolysis of the isopropylidene group to yield 1-β-D-ribofuranosyl-1,2,4-triazole-3-carboxamide.

SCHEME 1

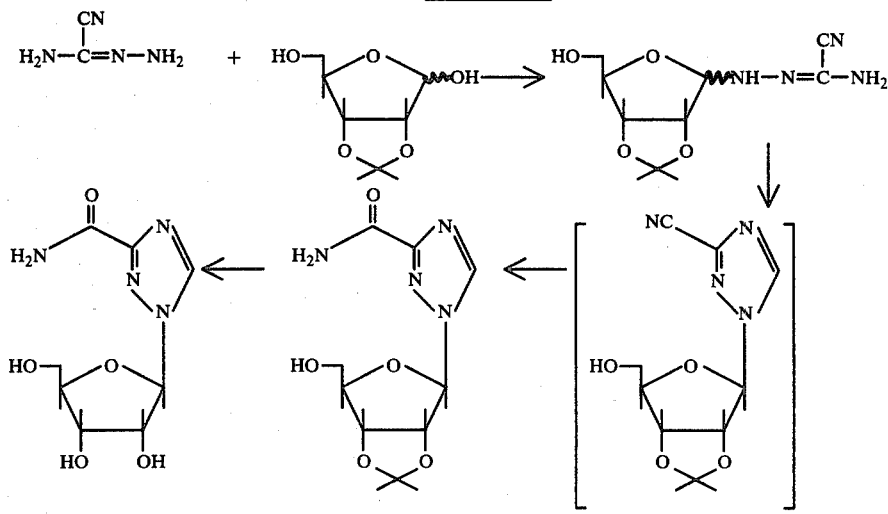

DETAILED DESCRIPTION OF THE INVENTION

Cyanoformimidic acid hydrazide is reacted with 2,3-O-isopropylidene-D-ribose and an acid catalyst in an appropriate solvent for several hours at room temperature to give $N^1$-(2,3-O-isopropylidene-D-ribofuranosyl) cyanoformamidrazone. Cyanoformimidic acid hydrazide is prepared as per J. Org. Chem. 26, 3783 (1961). Additionally it has been described in U.S. Pat. No. 3,004,060. 2,3-O-isopropylidene-D-ribose is prepared by conventional procedures from D-ribose and acetone. Suitable solvents are common organic solvents such as alcohols, ethers and hydrocarbons which will not enter into the reaction and in which the reactants are soluble. Representative examples include but are not necessary limited to methanol, ethanol, dioxane, tetrahydrofuran, dimethoxyethane, methoxyethanol and the like. Suitable acid catalysts for the condensation are mineral acids and organic acids which included but are not necessary limited to formic acid and anhydrous HCl and the like. While the reaction can be run at room temperatures it is of course understood that the reaction can be run at elevated temperatures up to and including the reflux temperature of the solvent. Higher temperatures will of course result in shorter reaction times. As will be evident to those skilled in the art, the time period necessary for the reactions is dependent upon factors such as temperature, solvent and catalyst. The values listed are representative only and should not be construed as limiting.

The triazole ring is formed from $N^1$-(2,3-O-isopropylidene-D-ribofuranosyl)-cyanoformamidrazone plus an additional reactant which contributes a one carbon fragment which is in the formic acid oxidization state. This ring closure reaction can be run with or without a catalyst. An anhydrous solvent can be used or optionally the carbon-donating reactant can serve as the solvent. Suitable as solvents are anhydrous ethers, alcohols and hydrocarbons as hereafore described. If a solvent is used, the reaction is run at from about 0° to the reflux temperature of the solvent. If no solvent is used it can be run from about 0° to about 80°. The reaction time is dependent upon the presence or absence of catalyst and solvent and on reaction temperature. Thus the reaction time is from about 5 minutes to 24 hours depending upon the other parameters and is not to be construed as limiting.

As representative examples of reactants which can supply the one carbon fragment for the triazole ring are triethylorthoformate, acetic-formic anhydride, dimethoxymethyl acetate, formic acid-formamide, dimethylformamide dimethyl acetal, and dimethylformamide-phosphoryl chloride and the like. The reaction can be run without a catalyst, however, the reaction will procede at a more facile rate in the presence of a catalyst. Suitable as catalysts are mineral acids and organic acid such as but not necessary limited to anhydrous HCl, anhydrous sulfuric, acetic, formic, bis(p-nitrophenyl) phosphate and p-tolunesulfonic acid.

The ring formation reaction thus yields 3-cyano-1-(2,3-O-isopropylidene-D-ribofuranosyl)-1,2,4-triazole. This product optionally can be isolated or it can be converted directly to the 3-carboxamide derivative. Both the α and β isomers are formed during the triazole ring formation reaction. The ratio of α to β is dependent on certain reaction parameters. Thus more β is produced as the rate of the reaction is increased. Using either triethylorthoformate or acetic-formic anhydride as both solvent and carbon atom donating reactant, at 20° after 24 hours the α/β ratio is ⅓. The addition of bis(p-nitrophenyl)phosphate to the triethylorthoformate reactions results in complete reaction in several hours with the α/β ratio being 1/10. The further addition of dioxane and a reaction temperature of 80° results in complete reaction in 10 minutes and a α/β ratio of <1/10.

The 3-cyano derivative is converted to the 3-carboxamide by hot aqueous ammonia. The usual procedure being heating the cyano derivative on a steam bath for about 1 to 2 hours in concentrated ammonium hydroxide.

The isopropylidene group is removed by conventional acid treatment. Representative examples being acetic acid at steam bath temperature or formic or trifluoroacetic acid at room temperature.

For the sake of example only, the hereafore reaction scheme has utilized an isopropylidene group as the blocking group on the 2,3-hydroxyls of the ribose moiety; however, it is understood that other blocking groups could be used. For example, benzylidene, p-methoxybenzylidene, ethoxymethylene or 2,3-cyclic carbonate blocking groups could also be utilized. Although we do not wish to be bound by theory, it is believed that the above mentioned blocking groups maintain the D-ribose sugar in the furanose configuration. This same configuration could also be maintained by blocking the 5-hydroxyl group of the D-ribose sugar with a blocking group such as a trityl ether group or the like. Thus D-ribose is blocked by conventional procedures with acetals, ethers and carbonates, such as but not limited to those hereafore described, and the blocked D-ribose is utilized in the reaction scheme in a manner analogous to that of 2,3-O-isopropylidene-D-ribose.

Although we do not wish to be bound by theory, it is believed that carboalkoxy-formimidic acid hydrazide or carbamoylformimidic acid hydrazide could also be utilized in place of cyanoformimidic acide hydrazide. These reagents are reacted with blocked D-ribose and then ring closed in a manner analogous with the cyano derivative to yield 3-carboalkoxy or 3-carboxamide-1-(blocked-D-ribofuranosyl)-1,2,4-triazole. In the case of 3-carboalkoxy, ammonolysis yields the 3-carboxamide. In either case, the 3-carboxamide compound is deblocked to yield the product.

In a preferred embodiment of the invention 1-β-D-ribofuranosyl-1,2,4-triazole-3-carboxamide is prepared by condensing cyanoformimidic acid hydrazide with 2,3-O-isopropylidene-D-ribose in anhydrous ethanol in the presence of 80% formic acid to give N'-(2,3-O-isopropylidene-D-ribofuranosyl)-cyanoformamidrazone, The cyanoformamidrazone is then ring closed with triethylorthoformate to give 3-cyano-1-(2,3-O-isopropylidene-β-D-ribofuranosyl)-1,2,4-triazole which is treated with hot aqueous ammonia followed by acidic removal of the isopropylidene blocking group with 80% trifluoroacetic acid.

As opposed to glycosylation procedures wherein both 3 and 5 isomers of 1-ribofuranosyl-1,2,4-triazoles, e.g. 3 or 5 cyano, are produced, an advantage of this invention is that only the biological active 3-isomer is produced.

As shown in patent 3,798,209, 1-β-D-ribofuranosyl-1,2,4-triazole-3-carboxamide is a broad spectrum antiviral showing in vitro antiviral activity against, inter alia, herpes virus, myxoma virus, vacccinia virus, adeno virus, parainfluenza virus and type 3 rhino virus.

Additional in vitro and in vivo antiviral activity is published in *Science*, 177, 705 (1972), the disclosure of which is herein expressly incorporated by reference.

The following preferred specific examples are given as representative examples of the invention and are to be construed as merely illustrative, and not limitative of the remainder of the disclosure of this invention. For the purpose of these examples 3-cyano-1-(2,3-O-isopropylidene-β-D-ribofuranosyl)-1,2,4-triazole can be isolated (example 2); however, isolation of the pure product is not necessary and this product can be used without isolation as per example 3.

Melting points were determined on a Thomas-Hoover apparatus and are uncorrected. Evaporations were accomplished with a rotating evaporator under reduced pressure with the bath temperature <35°. TLC plates were run with Woelm precoated silica gel plates eluting with $CHCl_3$-MeOH (9:1). Visualization was by uv lamp or a spray of 10% sulfuric acid and 1% p-anisaldehyde in methanol followed by gentle heating on a hot plate.

EXAMPLE 1

$N^1$-(2,3-O-isopropylidene-D-ribofuranosyl) cyanoformamidrazone 2,3-O-isopropylidene-D-ribose (1.80 g, 10 mmol) was dissolved in EtOH (50 ml). Cyanoformidic acid hydrazide (0.85 g, 10 mmol) and 88% formic acid (0.5 ml) were added and stirred over night at room temperature. The reaction mixture was adsorbed on silica gel (10 g) and applied to a silica gel column (100 g). The column was eluted with benzene (200 ml), 30% ethylether in benzene (1.5 l) and finally 40% ether in benzene. Fractions containing the product were combined and evaporated to give product which was crystallized from benzene-ether to yield 900 mg, mp 118°–120°. (Pmr shows the product contained ⅓ mole benzene) Recrystallization from the same mixed solvent and drying in vacuo gave pure product, mp 127°–128°.

Anal. Calcd for $C_{10}H_{16}N_4O_4$: C, 46.87; H, 6.29; N, 21.86. Found: C, 46.87; H, 6.47; N, 21.85.

On a larger scale, cyanoformimidic acid hydrazide (23.5 g, 123.8 mmol) and 2,3-O-isopropylidene-D-ribose (10.5 g, 123.8 mmol) in EtOH (500 ml) containing 88% formic acid (2 ml) was stirred 23 hours at room temp. Evaporation and crystallization of the residue from benzene-ether gave crystalline product (28.9 g, 80% yield). This material was suitable for subsequent reactions.

EXAMPLE 2

3-Cyano-1-(2,3-O-isopropylidene-D-ribofuranosyl)-1,2,4-triazole

The product of example 1 (500 mg, 1.75 mmol) was added to triethyl orthoformate (3½ ml) followed by bis(p-nitrophenyl)phosphate (25 mg). After 2 hours at room temp. the solvent was removed in vacuo. The residue dissolved in $CHCl_3$ was applied to a silica gel column (100 g) and the column was washed with $CHCl_3$ (1.5 l). Elution with 20% EtOAc in $CHCl_3$ (1 l) brought off the product. The corresponding fractions were evaporated to give 78% yield (360). The pmr spectrum shows the α/β ratio to be about 1:10. This oil can be used for the next reaction by treatment in a manner corresponding to the portions of example 3 after removal of the triethylorthoformate.

EXAMPLE 3

1-(2,3-O-Isopropylidene-β-D-ribofuranosyl)-1,2,4-triazole-3-carboxamide and
1-(2,3-O-isopropylidene-α-D-ribofuranosyl)-1,2,4-triazole-3-carboxamide.

Crude $N^1$-(2,3-O-isopropylidene-D-ribofuranosyl) cyanoformamidrazone from 10 mmoles of 2,3-O-isopropylidene-D-ribose was dissolved in triethyl orthoformate (15 ml). After 2 days the solvent was removed, the residue was dissolved in EtOH (25 ml) and conc. $NH_4OH$ (100 ml) added. The solution was heated on the steam bath for 1½ hr. The residue after evaporation was adsorbed on silica gel, applied to a silica gel column (100 g), and eluted with 10% MeOH in $CHCl_3$ collecting 15 ml fractions. Fractions 40–65 were combined, evaporated, and the residue crystallized from EtOH to give 230 mg (8%) of the α anomer with mp 245°–249°.

Anal. Calc for $C_{11}H_{16}N_4O_5$: C, 46.48; H, 4.67; N, 19.71. Found: C, 46.84; H, 5.80; N, 19.95.

The filtrate was evaporated and the residue crystallized from MeOH-EtOAc to give 650 mg (23%) of the β anomer with mp 154–156 in two crops.

Anal. Calc. for $C_{11}H_{16}N_4O_5$: C, 46.48; H, 4.67; N, 19.71. Found: C, 46.68; H, 5.94; N, 19.83.

1-α-D-Ribofuranosyl-1,2,4-triazole carboxamide 65 mg of the α anomer from example 3 was treated with 5 ml of 80% $F_3CCOOH$ for 10 min. and then evaporated to dryness. The residue was dissolved in water, filtered and freeze dried to give 54 mg of product.

1-β-D-Ribofuranosyl-1,2,4-triazole-3-carboxamide 150 mg of the β anomer from example 3 was treated with 5 ml 80% aqueous trifluoroacetic acid for 10 min. The solution was then evaporated and the product was crystallized from EtOH to give 111 mg of product with mp 165°–167°.

Anal. Calc for $C_8H_{12}N_4O_5$: C, 39.35; H, 4.95; N, 22.94. Found: C, 39.59; H, 4.82; N, 22.82

We claim:

1. A process for preparing 1-B-D-ribofuranosyl-1,2,4-triazole-3-carboxamide which comprises reacting cyanoformimidic acid hydrazide with ribose which is blocked with a blocking group chosen from the group consisting of isopropylidene, benzylidene, p-methoxybenzylidene, ethoxymethylene or 2,3-cyclic carbonate to from N'-(blocked ribofuranosyl)-cyanoformamidrazone which is ring closed with a one carbon atom donating reagent chosen from the group consisting of triethylorthoformate, aceticformic anhydride, dimethoxymethyl acetate, formic acid-foramide, dimethylforamide dimethyl acetal or dimethylforamide-phosphoryl chloride, to form 3-cyano-1-(blocked-B-D-ribofuranosyl)-1,2,4-triazole which is treated with ammonia to remove the blocking group to yield the product.

2. A process according to claim 1 for preparing 1-B-D-ribofuranosyl-1,2,4-triazole-3-carboxamide which comprises reacting cyanoformimidic acid hydrazide with 2,3-O-isopropylidene-D-ribose to form N'-(2,3-O-isopropylidene-D-ribfuranosyl)-cyanoformamidrazone which is ring closed with a one carbon atom donating reagent chosen from the group consisting of triethylorthoformate, acetic-formic anhydride, dimethoxymethyl acetate, formic acid-foramide, dimethylforamide dimethyl acetal or dimethylforamide-phosphoryl chloride to form 3-cyano-1-(2,3-O-isopropylidene-B-D-ribofuranosyl)-1,2,4-triazole which is treated with aqueous ammonia and the isopropylidene group removed to form the product.

3. The Process of claim 1 wherein the one carbon atom donating reagent is chosen from triethylorthoformate or acetic-formic anhydride.

4. The Process of claim 1 wherein the isopropylidene group is removed by treatment with acetic acid, formic acid or trifluoroacetic acid.

* * * * *